(12) United States Patent
Dong et al.

(10) Patent No.: US 10,219,545 B2
(45) Date of Patent: Mar. 5, 2019

(54) ELECTRONIC ATOMIZATION APPARATUS WITH SWITCH-CLOSED ATOMIZER AND ELECTRONIC SIMULATION CIGARETTE

(71) Applicant: SHENZHEN JINJIA TECHNOLOGIES CO., LTD, Shenzhen, Guangdong (CN)

(72) Inventors: Jihong Dong, Guangdong (CN); Chunmiao Hu, Guangdong (CN)

(73) Assignee: SHENZHEN JINJIA TECHNOLOGIES CO., LTD, Shenzhen (CN)

( * ) Notice: Subject to any disclaimer, the term of this patent is extended or adjusted under 35 U.S.C. 154(b) by 18 days.

(21) Appl. No.: 15/548,777

(22) PCT Filed: Jun. 7, 2016

(86) PCT No.: PCT/CN2016/085139
§ 371 (c)(1),
(2) Date: Aug. 4, 2017

(87) PCT Pub. No.: WO2017/016323
PCT Pub. Date: Feb. 2, 2017

(65) Prior Publication Data
US 2018/0027880 A1   Feb. 1, 2018

(30) Foreign Application Priority Data
Jul. 30, 2015   (CN) .......................... 2015 1 0457792

(51) Int. Cl.
A24F 47/00   (2006.01)
F16K 31/50   (2006.01)

(52) U.S. Cl.
CPC ............ *A24F 47/008* (2013.01); *F16K 31/50* (2013.01)

(58) Field of Classification Search
CPC ..................................................... A24F 47/008
(Continued)

(56) References Cited

U.S. PATENT DOCUMENTS

| 5,836,318 A | * | 11/1998 | Adams | ..................... A24F 13/24 |
| | | | | 131/253 |
| 2015/0027468 A1 | * | 1/2015 | Li | ......................... A24F 47/008 |
| | | | | 131/329 |
| 2015/0150306 A1 | * | 6/2015 | Chen | ..................... A24F 47/008 |
| | | | | 131/329 |

FOREIGN PATENT DOCUMENTS

| CN | 203633504 U | 6/2014 |
| CN | 205180357 U | 4/2016 |

OTHER PUBLICATIONS

1st Office Action of counterpart Chinese Patent Application No. 201510457792.X dated May 20, 2016.

(Continued)

*Primary Examiner* — Phuong Dinh

(57) ABSTRACT

An electronic atomization apparatus with a switch-closed atomizer and an electronic simulation cigarette are disclosed. The electronic atomization apparatus comprises a battery rod (10), an atomizer (20) arranged on a top end of the battery rod (10), an atomization liquid storage device (30), a sleeve (40) and a suction nozzle upper cover (50). When in use, the atomization liquid storage device is placed in the sleeve, and the suction nozzle upper cover is sleeved on the sleeve. The atomization liquid storage device is pushed to move down by rotating the suction nozzle upper cover, while the atomizer-abuts against a sealing rubber (35), so that the atomization liquid storage device and the sealing rubber (35) slide relative to each other in opposite directions, so as to open a liquid outlet (32) of the atomization liquid storage device to communicate with a liquid inlet (22) of the atomizer.

16 Claims, 3 Drawing Sheets

(58) Field of Classification Search
USPC .................................................. 131/328–329
See application file for complete search history.

(56) References Cited

OTHER PUBLICATIONS

2nd Office Action of counterpart Chinese Patent Application No. 201510457792A dated Dec. 14, 2016.

\* cited by examiner

ELECTRONIC ATOMIZATION APPARATUS WITH SWITCH-CLOSED ATOMIZER AND ELECTRONIC SIMULATION CIGARETTE

TECHNICAL FIELD

The present disclosure relates to the technical field of electronic simulation cigarettes, and more particularly, relates to an electronic atomization apparatus with a switch-closed atomizer and an electronic simulation cigarette.

BACKGROUND

Electronic cigarette, also known as electronic simulation cigarette, is a kind of electronic products simulating a cigarette, and is similar to the cigarette in aspects of appearance, smoke, taste and feeling. The electronic cigarette is the product which is sucked in by a user after turning nicotine into a steam by means of atomization or the like. In general, the electronic simulation cigarette substantially comprises a battery rod and an atomizer cartridge. The atomizer is a heating element in configuration; tobacco tar inside the atomizer will be heated and atomized when being powered by the battery, and thus it is possible to achieve an effect of "blowing smoke" during the sucking. The composition of the smoke may be preset to form corresponding taste of the cigarette without containing any harmful component. The existing electronic simulation cigarette has a complicated structure and is inconvenient in production. Besides, the sealing effect of the electronic simulation cigarette is poor; the tobacco tar can be only stored for a relative short period of time, and thus the tobacco tar needs to be added manually using a tobacco tar bottle. Further, the tobacco tar is prone to leak out of the atomizer, and the user experience is poor.

Therefore, the electronic cigarette in the art needs to be improved and further developed.

SUMMARY

Aiming at the defects described above in the prior art, the technical problem which the present disclosure mainly solves is to provide an electronic atomization apparatus with a switch-closed atomizer and an electronic simulation cigarette, which is intended to solve the technical problems in the prior art that the sealing effect of the electronic simulation cigarette is bad, and the user experience is poor.

The technical solution provided in the present disclosure to solve the technical problems is as follow:

An electronic atomization apparatus with a switch-closed atomizer, comprising: a battery rod, an atomization liquid storage device configured for storing atomization liquid, a suction nozzle upper cover and a hollow gas guide tube; wherein an atomizer and a sleeve sleeved on an outside of the atomizer are arranged on a top end of the battery rod; the atomizer is provided with a heating and atomizing element configured for atomizing the atomization liquid.

At least one liquid inlet of the atomizer allowing the atomization liquid inside the atomization liquid storage device to flow to the atomizer is further provided on the atomizer; a sliding cavity formed by recessing inwardly is arranged in the atomization liquid storage device; at least one liquid outlet of the atomization liquid storage device allowing the atomization liquid in the atomization liquid storage device to flow to the atomizer is correspondingly formed in the sliding cavity; one end of the atomization liquid storage device that is opposite to the sliding cavity is provided with an opening, and a sealing cover is arranged on the opening; the other end of the atomization liquid storage device is connected to the sealing cover via the hollow gas guide tube and further communicated with atmosphere.

A spring is provided in the sliding cavity, and a slidable sealing rubber is arranged on the spring; the sealing rubber is hollow, allowing the smoke to flow through; one end of the sealing rubber is connected to the spring, while the other end of the sealing rubber is in contact with a top end of the atomizer when the atomization liquid storage device is placed into the sleeve.

When using the electronic atomization apparatus having a switch-closed atomizer, the atomization liquid storage device is placed into the sleeve, and the suction nozzle upper cover is sleeved on the sleeve; the atomization liquid storage device is pushed to move downwardly by rotating the suction nozzle upper cover, meanwhile the top end of the atomizer abuts against the sealing rubber; the atomization liquid storage device and the sealing rubber slide relative to each other in opposite directions, so that the liquid outlet of the atomization liquid storage device is opened to communicate with the liquid inlet of the atomizer.

In the electronic atomization apparatus with a switch-closed atomizer, an inner rotary lifting mechanism and a pressing element are arranged on a top end of the suction nozzle upper cover; when stopping using the atomizer, the pressing element is lifted up via the inner rotary lifting mechanism arranged on the top end of the suction nozzle upper cover to form a gap and a distance therebetween, meanwhile the spring in the sliding cavity jacks up the atomization liquid storage device, in such a way that the sealing rubber of the sliding cavity slides to the liquid outlet of the atomization liquid storage device, and thus the liquid outlet of the atomization liquid storage device is sealed off.

When using the atomizer again, the inner rotary lifting mechanism arranged on the top end of the suction nozzle upper cover is rotated in an opposite direction, pushing the atomization liquid storage device to move downwardly, and the sealing rubber in the sliding cavity is abutted against the atomizer; the liquid outlet of the atomization liquid storage device moves away from the sealing rubber, and the liquid outlet of the atomization liquid storage device is opened to communicate with the liquid inlet of the atomizer.

In the electronic atomization apparatus with a switch-closed atomizer, a positioning buckle is arranged on an inner wall of the sleeve, and a positioning groove matching with the positioning buckle is arranged on an outer wall of the atomization liquid storage device correspondingly.

In the electronic atomization apparatus with a switch-closed atomizer, a control unit configured for controlling the heating and atomizing element is further provided between the battery rod and the atomizer; the battery rod is connected to the heating and atomizing element via the control unit.

In the electronic atomization apparatus with a switch-closed atomizer, two liquid outlets of the atomization liquid storage device allowing the atomization liquid in the atomization liquid storage device to flow to the atomizer are symmetrically arranged on a side wall of the sliding cavity.

In the electronic atomization apparatus with a switch-closed atomizer, the hollow gas guide tube successively runs through the atomization liquid storage device and the sealing cover thereof; one end of the hollow gas guide tube is communicated with the atomizer, while the other end of the hollow gas guide tube is communicated with the suction nozzle upper cover; the hollow gas guide tube is configured for leading out the atomized smoke.

In the electronic atomization apparatus with a switch-closed atomizer, the inner rotary lifting mechanism comprises: a rotation portion configured for receiving the rotation operations of a user; a nut is further provided on the rotation portion; a pressing element and a bolt matching with the nut are further provided on a movable portion.

In the electronic atomization apparatus with a switch-closed atomizer, the movable portion is fixedly connected to the pressing element; while the pressing element is in contact with the sealing cover of the atomization liquid storage device via the sleeve.

An electronic simulation cigarette is provided, which comprises the electronic atomization apparatus as is described above.

The present disclosure provides an electronic atomization apparatus having a switch-closed atomizer and an electronic simulation cigarette, effectively solving the technical problems in the prior art that the sealing effect of the electronic simulation cigarette is bad, the user experience is poor, and the usage is inconvenient. The electronic atomization apparatus comprises a battery rod, an atomization liquid storage device configured for storing atomization liquid, a suction nozzle upper cover and a hollow gas guide tube; wherein an atomizer and a sleeve sleeved on an outside of the atomizer are arranged on a top end of the battery rod; the atomizer is provided with a heating and atomizing element configured for atomizing the atomization liquid; at least one liquid inlet of the atomizer allowing the atomization liquid inside the atomization liquid storage device to flow to the atomizer is further provided on the atomizer; a sliding cavity formed by recessing inwardly is arranged in the atomization liquid storage device; at least one liquid outlet of the atomization liquid storage device allowing the atomization liquid in the atomization liquid storage device to flow to the atomizer is correspondingly formed in the sliding cavity; one end of the atomization liquid storage device that is opposite to the sliding cavity is provided with an opening, and a sealing cover is arranged on the opening; the other end of the atomization liquid storage device is connected to the sealing cover via the hollow gas guide tube and further communicated with atmosphere; a spring is provided in the sliding cavity, and a slidable sealing rubber is arranged on the spring; the sealing rubber is hollow, allowing the smoke to flow through; one end of the sealing rubber is connected to the spring, while the other end of the sealing rubber is in contact with a top end of the atomizer when the atomization liquid storage device is placed into the sleeve; when using the electronic atomization apparatus having a switch-closed atomizer, the atomization liquid storage device is placed into the sleeve, and the suction nozzle upper cover is sleeved on the sleeve; the atomization liquid storage device is pushed to move downwardly by rotating the suction nozzle upper cover, meanwhile the top end of the atomizer abuts against the sealing rubber; the atomization liquid storage device and the sealing rubber slide relative to each other in opposite directions, so that the liquid outlet of the atomization liquid storage device is opened to communicate with the liquid inlet of the atomizer. The atomization liquid storage device is pushed to move downwardly by rotating the suction nozzle upper cover, meanwhile the top end of the atomizer abuts against the sealing rubber; the atomization liquid storage device and the sealing rubber slide relative to each other in opposite directions, so that the liquid outlet of the atomization liquid storage device is opened to communicate with the liquid inlet of the atomizer, and thus the atomization liquid in the atomization liquid storage device flows to the liquid inlet of the atomizer. The method described above improves the sealing effect; in this way, the tobacco tar can be stored for a long period of time, and the tobacco tar will not be leaked out easily. The atomization liquid storage device is opened and closed by rotation to control the atomization liquid to flow out when it is needed, and control the atomization liquid storage device to close in a contrary case. In this way, it is possible to keep the atomization liquid remain fresh. It is convenient for the user to operate, and the structure thereof is simple and easy to the use, which brings great convenience to the user.

DETAILED DESCRIPTION

An electronic atomization apparatus with a switch-closed atomizer and an electronic simulation cigarette are provided in the present disclosure. In order to make the objective, the technical solution and the advantages of the present disclosure described more clearly and explicitly, the present disclosure will be described in detail with reference to the drawings and embodiments. It should be understood that, the specific embodiments described herein are merely for explanation, not for limitation.

Figure 1:
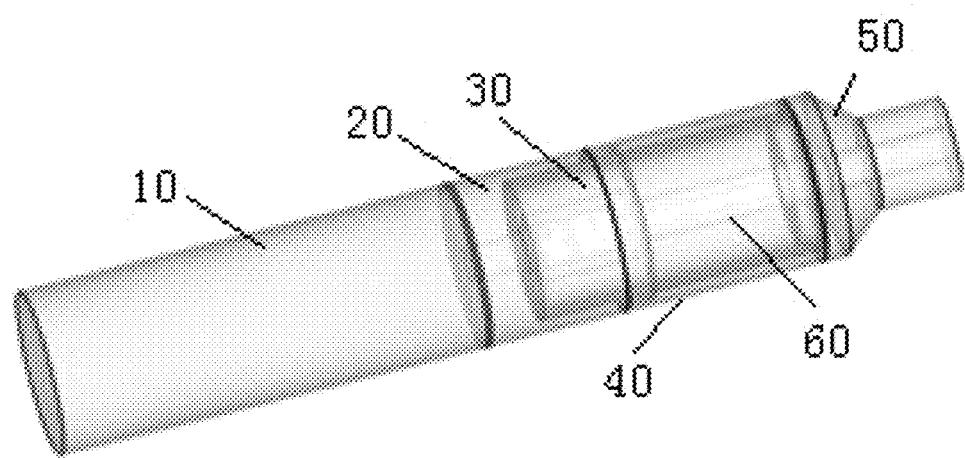
FIG. 1 is a stereogram of a preferred embodiment of an electronic simulation cigarette of the present disclosure.

Referring to FIG. 1, a stereogram of a preferred embodiment of an electronic simulation cigarette of the present disclosure is depicted. As is shown in FIG. 1, the electronic simulation cigarette of the present disclosure may comprise: a battery rod 10, an atomizer 20 arranged on a top end of the battery rod 10, an atomization liquid storage device 30 configured for storing atomization liquid, a sleeve 40 and a suction nozzle upper cover 50. In this case, the battery rod 10, the atomizer 20 arranged on a top end of the battery rod 10, the atomized liquid storage device 30 configured for storing atomization liquid, the sleeve 40 and the suction nozzle upper cover 50 are arranged successively.

Figure 2:
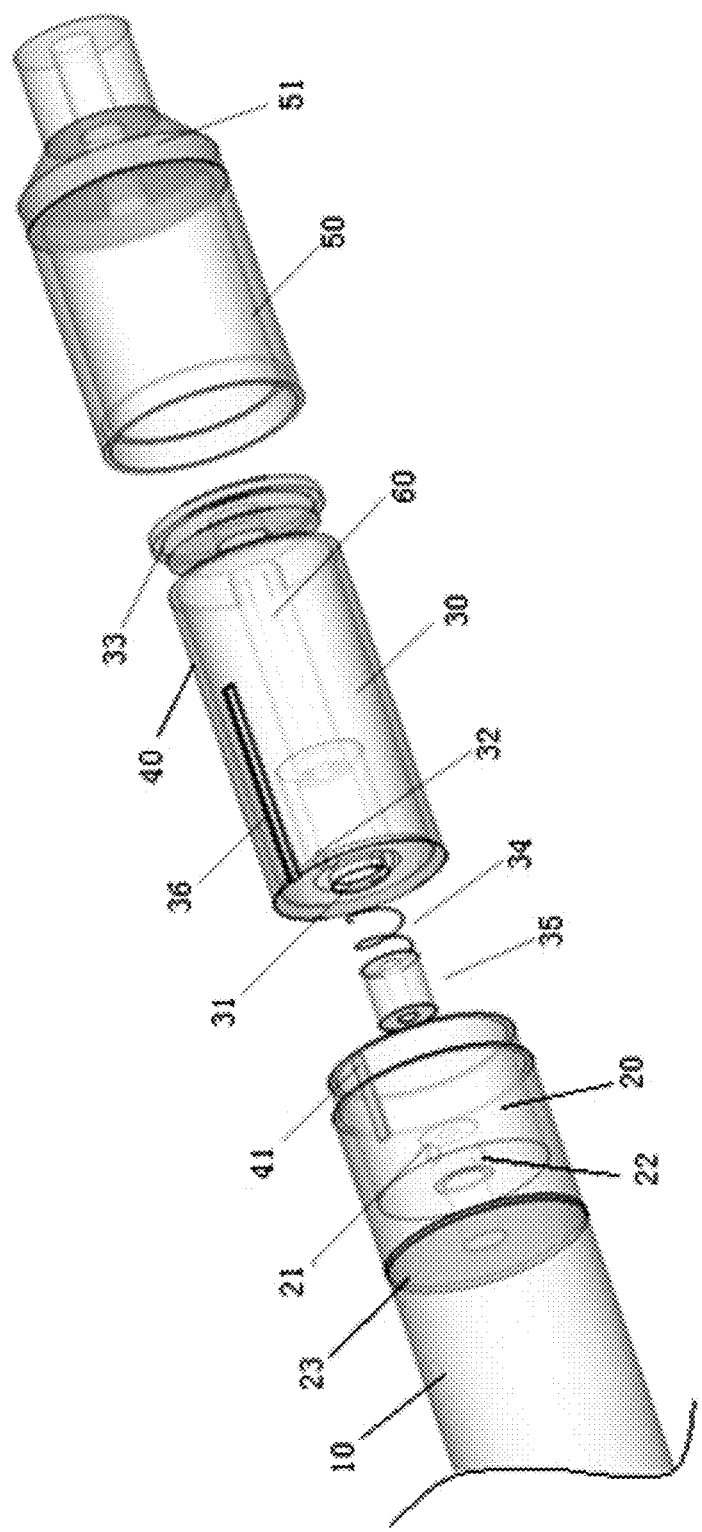
FIG. 2 is an explored view of a preferred embodiment of an electronic atomization apparatus having a switch-closed atomizer of the present disclosure.

The electronic simulation cigarette of the present disclosure is improved in the structure. FIG. 1 shows an over-all structure thereof, and can not reflect the innovation of the present disclosure. In order to specifically explain the innovation of the present disclosure, FIG. 2 is provided, wherein FIG. 2 is an explored view of a preferred embodiment of an electronic atomization apparatus having a switch-closed atomizer of the present disclosure. As is shown in FIG. 2, the electronic atomization apparatus having a switch-closed atomizer may comprise: a battery rod 10, an atomization liquid storage device 30 configured for storing the atomization liquid, a suction nozzle upper cover 50 and a hollow gas guide tube 60. An atomizer 20 and a sleeve 40 sleeved on an outside of the atomizer 20 are arranged on a top end of the battery rod 10. The atomizer 20 is provided with a heating and atomizing element 21 configured for atomizing the atomization liquid. The heating and atomizing element 21 is connected to the battery rod 10. That is, the battery rod 10 supplies power to the heating and atomizing element 21. The heating and atomizing element 21 emits heat to atomize the atomization liquid.

At least one liquid inlet 22 of the atomizer allowing the atomization liquid inside the atomization liquid storage device 30 to flow to the atomizer 20 is further provided on the atomizer 20. A sliding cavity 31 formed by recessing inwardly is arranged in the atomization liquid storage device 30. At least one liquid outlet 32 of the atomization liquid storage device allowing the atomization liquid in the atomization liquid storage device 30 to flow to the atomizer 20 is correspondingly formed in the sliding cavity 31. One end of the atomization liquid storage device 30 that is opposite to the sliding cavity 31 is provided with an opening, and a sealing cover 33 is arranged on the opening. The other end of the atomization liquid storage device 30 is connected to the sealing cover 33 via the hollow gas guide tube 60, and further communicated with atmosphere. The upper end of the atomization liquid storage device is sealed by the sealing cover in order to prevent the atomization liquid from flowing out.

A spring 34 is provided in the sliding cavity 31, and a slidable sealing rubber 35 is further arranged on the spring 34. The sealing rubber 35 is hollow, allowing the smoke to flow through. In this case, one end of the sealing rubber 35 is connected to the spring 34, while the other end of the sealing rubber 35 is in contact with the top end of the atomizer 20 when the atomization liquid storage device 30 is placed into the sleeve 40.

When using the electronic atomization apparatus having a switch-closed atomizer, the atomization liquid storage device 30 is placed into the sleeve 40, and the suction nozzle upper cover 50 is sleeved on the sleeve 40. The atomization liquid storage device 30 is pushed to move downwardly by rotating the suction nozzle upper cover 50, meanwhile the top end of the atomizer 20 abuts against the sealing rubber 35. In this way, the atomization liquid storage device 30 and the sealing rubber 35 slide relative to each other in opposite directions, so as to open the liquid outlet 32 of the atomization liquid storage device to communicate with the liquid inlet 22 of the atomizer.

In specific, the sealing rubber 35 is slidable in the sliding cavity 31. The sliding cavity 31 of the atomization liquid storage device of the present disclosure is optionally in shape of a cylinder. A cross-section of the sealing rubber 35 matches with the sliding cavity 31, while a length of the sealing rubber 35 is smaller than that of the sliding cavity 31. Furthermore, the liquid outlet 32 of the atomization liquid storage device is arranged on a side wall of the sliding cavity 31 that is close to the atomizer 20. In practical application, the sealing rubber 35 is hollow, so that the smoke can easily pass through. The sealing rubber 35 may be fixedly connected to the atomizer 20, or may be in contact with the surfaces of the atomizer 20. The connection between the sealing rubber and the atomizer may be achieved by a plurality of ways. The battery rod 10 is configured for supplying power, and it belongs to the prior art.

The atomization liquid storage device 30 is pushed to move downwardly by rotating the suction nozzle upper cover 50, meanwhile the top end of the atomizer 20 abuts against the sealing rubber 35. In this way, the atomization liquid storage device 30 and the sealing rubber 35 slide relative to each other in opposite directions. In this way, the liquid outlet 32 of the atomization liquid storage device is opened and is further communicate with the liquid inlet 22 of the atomizer, and thus the atomization liquid in the atomization liquid storage device 30 may flow to the atomizer 20. This is exactly the working principle of opening and closing the atomization liquid storage device 30 by rotation. In this way, the electronic simulation cigarette is easy to use by the user, the operation is more convenient, and the user experience may be improved.

In the present disclosure, the atomization liquid storage device is separated from the atomizer, and thus the atomization liquid will not be in contact with the components (such as metal heating wires, or the like) inside the atomizer, and the atomization liquid may be sealed separately and stored for a long period of time. When the user is sucking the electronic simulation cigarette, the smoke flowing out of the atomizer may be directly delivered to the user via a hollow gas hole of the sealing rubber and the hollow gas guide tube in the sliding cavity of the atomization liquid storage device, and the user experience may be better. The atomization liquid storage device and the sealing rubber in the sliding cavity of the atomization liquid storage device may be slide relative to each other by rotation to open or close the liquid outlet of the atomization liquid storage device, ensuring that the atomization liquid in the atomization liquid storage device can be sealed when not in use to remain fresh. Furthermore, it is convenient for the user to operate, and the structure of the electronic simulation cigarette is simple and easy to use, and it may bring great convenience to the user.

Figure 3:
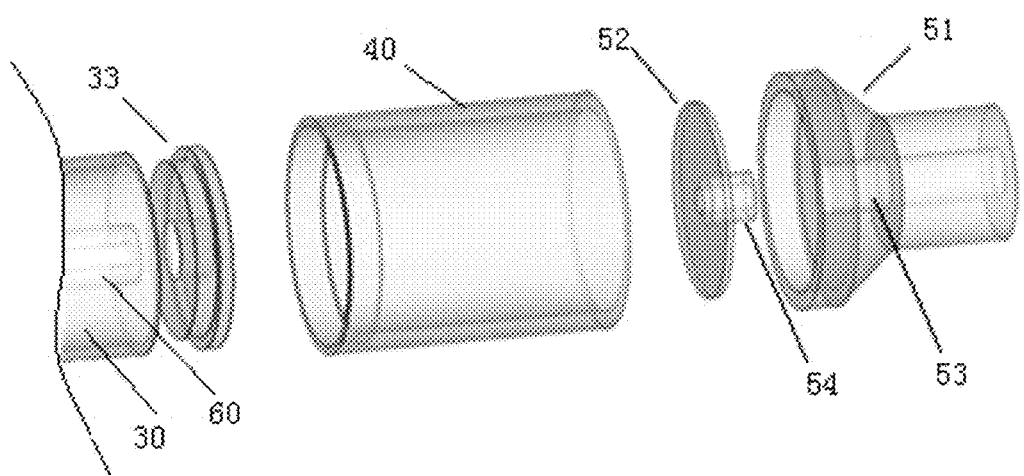
FIG. 3 is an explored view of a rotary lifting mechanism of the electronic atomization apparatus having a switch-closed atomizer of the present disclosure.

Furthermore, as is shown in FIG. 2 and FIG. 3, an inner rotary lifting mechanism 51 and a pressing element 52 are arranged on the top end of the suction nozzle upper cover 50. When stopping using the atomizer 20, the pressing element 52 is lifted up via the inner rotary lifting mechanism 51 arranged on the top end of the suction nozzle upper cover 50 to form a gap and a distance therebetween, meanwhile the spring 34 in the sliding cavity 31 jacks up the atomization liquid storage device 30, in such a way that the sealing rubber 35 of the sliding cavity 31 slides to the liquid outlet 32 of the atomization liquid storage device, and thus the liquid outlet of the atomization liquid storage device is sealed off.

When using the atomizer 20 again, the inner rotary lifting mechanism 51 arranged on the top end of the suction nozzle upper cover 50 is rotated in an opposite direction, pushing the atomization liquid storage device 30 to move downwardly, and the sealing rubber 35 in the sliding cavity 31 is abutted against the atomizer 20. In this way, the liquid outlet 32 of the atomization liquid storage device moves away from the sealing rubber 35, and thus the liquid outlet 32 of the atomization liquid storage device is opened, and further communicated with the liquid inlet 22 of the atomizer.

In general, when using the electronic atomization apparatus of the present disclosure, the atomization liquid storage device 30 is lowered down by rotating the inner rotary lifting mechanism 51, and the top end of the atomizer 20 abuts against the sealing rubber 35. In this way, the atomization liquid storage device 30 and the sealing rubber 35 slides relative to each other in opposite directions; the liquid outlet 32 of the atomization liquid storage device is opened, and further communicated with the liquid inlet 22 of the atomizer. After that, the heating and atomizing element 21 atomizes the atomization liquid, and the atomized smoke is delivered to the user for suction via the hollow gas guide tube 60.

When the electronic atomization apparatus of the present disclosure is stopped using, the atomization liquid storage device 30 is lifted up by rotating the inner rotary lifting mechanism 51, the spring 34 in the sliding cavity 31 jacks up the atomization liquid storage device 30. In this way, the sealing rubber 35 of the sliding cavity 31 slides to the liquid outlet 32 of the atomization liquid storage device, and thus the liquid outlet of the atomization liquid storage device is sealed off.

In practical application, it is also possible to use a longer spring 34 to replace the spring 34 and the sealing rubber 35 arranged in the sliding cavity 31 of the atomizer, in order to open or close the atomization liquid storage device 30. The working principle of the longer spring is contrary to that of the present disclosure. However, it may be easily thought of by one skilled in the art based on the principle of the present disclosure, and belong to an equivalent modification of the technical solution of the present disclosure. Therefore, this technical solution also belongs to the protection scope of the present disclosure.

Optionally, two liquid outlets 32 of the atomization liquid storage device allowing the atomization liquid in the atomization liquid storage device 30 to flow to the atomizer 20 are symmetrically arranged on the side wall of the sliding cavity 31. Of course, in practical application, it is also possible to arrange a plurality of liquid outlets 32. Preferably, two liquid outlets are provided for acquiring appropriate flow rate of the liquid. Likewise, it is possible to arrange a plurality of liquid inlets 22 allowing the atomization liquid in the atomization liquid storage device to flow to the atomizer in the atomizer 20.

Optionally, a positioning buckle 41 may be arranged on an inner wall of the sleeve 40, and a positioning groove 36 matching with the positioning buckle 41 may be arranged on an outer wall of the atomization liquid storage device 30 correspondingly. By the matching of these two elements, it is possible to achieve a positioning of the sleeve and the atomization liquid storage device 30, in order to ensure that the liquid inlet 22 may be communicated with the liquid outlet 32.

Optionally, a control unit 23 configured for controlling the heating and atomizing element 21 is further provided between the battery rod 10 and the atomizer 20. The battery rod 10 is connected to the heating and atomizing element 21 via the control unit 23.

Optionally, the hollow gas guide tube 60 successively runs through the atomization liquid storage device 30 and the sealing cover 33 thereof. One end of the hollow gas guide tube 60 is communicated with the atomizer 20, while the other end of the hollow gas guide tube 60 is communicated with the suction nozzle upper cover 50; the hollow gas guide tube is configured for leading out the atomized smoke. In fact, the hollow gas guide tube 60 is an output tube for the smoke; that is, the hollow gas guide tube leads out the atomized smoke for the user to suck in. The outlet of the hollow gas guide tube 60 is arranged in the suction nozzle upper cover 50, and the inner rotary lifting mechanism 51 is also arranged in the suction nozzle upper cover 50.

The inner rotary lifting mechanism 51 may be achieved in many ways, and the implementation may be illustrated by example. Referring to FIG. 3, FIG. 3 is an explored view of a rotary lifting mechanism of the electronic atomization apparatus having a switch-closed atomizer of the present disclosure. Optionally, the inner rotary lifting mechanism 51 may comprise: a rotation portion 53 configured for receiving the rotation operations of the user, and a movable portion 54 configured for moving the atomization liquid storage device 30 up and down. A nut is further provided on the rotation portion 53; a pressing element 52 and a bolt matching with the nut are further provided on the movable portion 54. The movable portion 54 is in contact with the atomization liquid storage device 30. In practical application, the rotation portion 53 is integrated with the suction nozzle upper cover 50; that is, the user may only need to rotate the suction nozzle upper cover 50. The conversion of the rotation to the up-down movement may be achieved by configuration of the bolt and the nut. By rotating the nut or the bolt, it is possible to achieve the up-down movement of the bolt or the nut. In this case, only one of the examples is given here for explanation.

Optionally, the movable portion 54 is fixedly connected to the pressing element 52, while the pressing element 52 is in contact with the sealing cover 33 of the atomization liquid storage device 30 via the sleeve 40. That is to say, the sleeve 40 is arranged between the sealing cover 33 of the atomization liquid storage device 30 and the suction nozzle upper cover 50.

In practical application, the appearance of the electronic atomization apparatus having a switch-closed atomizer of the present disclosure is similar to the cigarette, and thus there is little difference between the appearance of the electronic simulation cigarette and the real cigarette, and the simulation effect is good.

Based on the electronic atomization apparatus having a switch-closed atomizer of the present disclosure, an electronic simulation cigarette is further provided in the present disclosure, and the electronic simulation cigarette comprises the electronic atomization apparatus as is described above.

In conclusion, the present disclosure provides an electronic atomization apparatus having a switch-closed atomizer and an electronic simulation cigarette. The electronic atomization apparatus comprises a battery rod, an atomizer arranged on the top end of the battery rod, an atomization liquid storage device, a sleeve and a suction nozzle upper cover. When using the electronic atomization apparatus, the atomization liquid storage device is placed into the sleeve, and the suction nozzle upper cover is sleeved on the sleeve. The atomization liquid storage device is pushed to move downwardly by rotating the suction nozzle upper cover, meanwhile the top end of the atomizer abuts against the sealing rubber. In this way, the atomization liquid storage device and the sealing rubber slide relative to each other in opposite directions, so as to open the liquid outlet of the atomization liquid storage device to communicate with the liquid inlet of the atomizer. The atomization liquid storage device is separated from the atomizer, in such a way that the atomization liquid will not be in contact with the components (such as metal heating wires, or the like) inside the atomizer, and the atomization liquid may be sealed separately and stored for a long period of time. When the user is sucking the electronic simulation cigarette, the smoke flowing out of the atomizer may be directly delivered to the user via a hollow gas hole of the sealing rubber and the hollow gas guide tube in the sliding cavity of the atomization liquid storage device, and the user experience may be better. The atomization liquid storage device and the sealing rubber in the sliding cavity of the atomization liquid storage device may be slide relative to each other by rotation to open or close the liquid outlet of the atomization liquid storage device, ensuring that the atomization liquid in the atomization liquid storage device can be sealed when not in use to remain fresh. Furthermore, it is convenient for the user to operate, and the structure thereof is simple and easy to use, and it may bring brings great convenience to the user. The method described above improves the sealing effect; in this way, the tobacco tar can be stored for a long period of time, and the tobacco tar will not be leaked out easily. The atomization liquid storage device is opened and closed by rotation to control the flowing out of the atomization liquid; in this way, it is convenient for the user to operate, and the structure thereof is simple and easy to use, which brings great convenience to the user. In particular, the electronic atomization apparatus provided in the present disclosure has a much simpler structure and is convenient to manufacture.

Gas may be circulated in the electronic atomization apparatus, and the effect may be better. The atomization liquid storage device may be opened and closed by rotating the suction nozzle upper cover, and thus it is convenient to store and carry.

It should be understood that, the application of the present disclosure should not be limited to the examples described above. One skilled in the art may make many improvements and modifications based on the description above. All these belong to the protection scope of the claims of the present disclosure.

What is claimed is:

1. An electronic atomization apparatus with a switch-closed atomizer, comprising: a battery rod, an atomization liquid storage device configured for storing atomization liquid, a suction nozzle upper cover and a hollow gas guide tube; wherein an atomizer and a sleeve sleeved on an outside of the atomizer are arranged on a top end of the battery rod; the atomizer is provided with a heating and atomizing element configured for atomizing the atomization liquid;

at least one liquid inlet of the atomizer allowing the atomization liquid inside the atomization liquid storage device to flow to the atomizer is further provided on the atomizer; a sliding cavity formed by recessing inwardly is arranged in the atomization liquid storage device; at least one liquid outlet of the atomization liquid storage device allowing the atomization liquid in the atomization liquid storage device to flow to the atomizer is correspondingly formed in the sliding cavity; one end of the atomization liquid storage device that is opposite to the sliding cavity is provided with an opening, and a sealing cover is arranged on the opening; the other end of the atomization liquid storage device is connected to the sealing cover via the hollow gas guide tube and further communicated with atmosphere;

a spring is provided in the sliding cavity, and a slidable sealing rubber is arranged on the spring; the sealing rubber is hollow, allowing the smoke to flow through; one end of the sealing rubber is connected to the spring, while the other end of the sealing rubber is in contact with a top end of the atomizer when the atomization liquid storage device is placed into the sleeve;

when using the electronic atomization apparatus having the switch-closed atomizer, the atomization liquid storage device is placed into the sleeve, and the suction nozzle upper cover is sleeved on the sleeve; the atomization liquid storage device is pushed to move downwardly by rotating the suction nozzle upper cover, meanwhile the top end of the atomizer abuts against the sealing rubber; the atomization liquid storage device and the sealing rubber slide relative to each other in opposite directions, so that the liquid outlet of the atomization liquid storage device is opened to communicate with the liquid inlet of the atomizer.

2. The electronic atomization apparatus with the switch-closed atomizer of claim 1, wherein an inner rotary lifting mechanism and a pressing element are arranged on a top end of the suction nozzle upper cover; when stopping using the atomizer, the pressing element is lifted up via the inner rotary lifting mechanism arranged on the top end of the suction nozzle upper cover to form a gap and a distance therebetween, meanwhile the spring in the sliding cavity jacks up the atomization liquid storage device, in such a way that the sealing rubber of the sliding cavity slides to the liquid outlet of the atomization liquid storage device, and thus the liquid outlet of the atomization liquid storage device is sealed off;

when using the atomizer again, the inner rotary lifting mechanism arranged on the top end of the suction nozzle upper cover is rotated in an opposite direction, pushing the atomization liquid storage device to move downwardly, and the sealing rubber in the sliding cavity is abutted against the atomizer; the liquid outlet of the atomization liquid storage device moves away from the sealing rubber, and the liquid outlet of the atomization liquid storage device is opened to communicate with the liquid inlet of the atomizer.

3. The electronic atomization apparatus with the switch-closed atomizer of claim 1, wherein a positioning buckle is arranged on an inner wall of the sleeve, and a positioning groove matching with the positioning buckle is arranged on an outer wall of the atomization liquid storage device correspondingly.

4. The electronic atomization apparatus with the switch-closed atomizer of claim 1, wherein a control unit configured for controlling the heating and atomizing element is further provided between the battery rod and the atomizer; the battery rod is connected to the heating and atomizing element via the control unit.

5. The electronic atomization apparatus with the switch-closed atomizer of claim 1, wherein two liquid outlets of the atomization liquid storage device allowing the atomization liquid in the atomization liquid storage device to flow to the atomizer are symmetrically arranged on a side wall of the sliding cavity.

6. The electronic atomization apparatus with the switch-closed atomizer of claim 1, wherein the hollow gas guide tube successively runs through the atomization liquid storage device and the sealing cover thereof; one end of the hollow gas guide tube is communicated with the atomizer, while the other end of the hollow gas guide tube is communicated with the suction nozzle upper cover; the hollow gas guide tube is configured for leading out the atomized smoke.

7. The electronic atomization apparatus with the switch-closed atomizer of claim 1, wherein the inner rotary lifting mechanism comprises: a rotation portion configured for receiving the rotation operations of a user; a nut is further provided on the rotation portion; a pressing element and a bolt matching with the nut are further provided on a movable portion.

8. The electronic atomization apparatus with the switch-closed atomizer of claim 7, wherein the movable portion is fixedly connected to the pressing element; while the pressing element is in contact with the sealing cover of the atomization liquid storage device via the sleeve.

9. An electronic simulation cigarette, comprising the electronic atomization apparatus of claim 1.

10. The electronic simulation cigarette of claim 9, wherein an inner rotary lifting mechanism and a pressing element are arranged on a top end of the suction nozzle upper cover; when stopping using the atomizer, the pressing element is lifted up via the inner rotary lifting mechanism arranged on the top end of the suction nozzle upper cover to form a gap and a distance therebetween, meanwhile the spring in the sliding cavity jacks up the atomization liquid storage device, in such a way that the sealing rubber of the sliding cavity slides to the liquid outlet of the atomization liquid storage device, and thus the liquid outlet of the atomization liquid storage device is sealed off;

when using the atomizer again, the inner rotary lifting mechanism arranged on the top end of the suction nozzle upper cover is rotated in an opposite direction, pushing the atomization liquid storage device to move downwardly, and the sealing rubber in the sliding cavity is abutted against the atomizer; the liquid outlet of the atomization liquid storage device moves away from the sealing rubber, and the liquid outlet of the atomization liquid storage device is opened to communicate with the liquid inlet of the atomizer.

11. The electronic simulation cigarette of claim 9, wherein a positioning buckle is arranged on an inner wall of the sleeve, and a positioning groove matching with the positioning buckle is arranged on an outer wall of the atomization liquid storage device correspondingly.

12. The electronic simulation cigarette of claim 9, wherein a control unit configured for controlling the heating and atomizing element is further provided between the battery rod and the atomizer; the battery rod is connected to the heating and atomizing element via the control unit.

13. The electronic simulation cigarette of claim 9, wherein two liquid outlets of the atomization liquid storage device allowing the atomization liquid in the atomization liquid storage device to flow to the atomizer are symmetrically arranged on a side wall of the sliding cavity.

14. The electronic simulation cigarette of claim 9, wherein the hollow gas guide tube successively runs through the atomization liquid storage device and the sealing cover thereof; one end of the hollow gas guide tube is communicated with the atomizer, while the other end of the hollow gas guide tube is communicated with the suction nozzle upper cover; the hollow gas guide tube is configured for leading out the atomized smoke.

15. The electronic simulation cigarette of claim 9, wherein the inner rotary lifting mechanism comprises: a rotation portion configured for receiving the rotation operations of a user; a nut is further provided on the rotation portion; a pressing element and a bolt matching with the nut are further provided on a movable portion.

16. The electronic simulation cigarette of claim 15, wherein the movable portion is fixedly connected to the pressing element; while the pressing element is in contact with the sealing cover of the atomization liquid storage device via the sleeve.

* * * * *